United States Patent [19]

Ueyama et al.

[11] Patent Number: 4,898,833

[45] Date of Patent: Feb. 6, 1990

[54] METHOD FOR MEASURING CELL COUNTS AND/OR METHANE PRODUCING ACTIVITY OF METHANOGENS

[75] Inventors: Satoshi Ueyama; Satoru Isoda, Hyogo, both of Japan

[73] Assignee: Mitsubishi Denki Kabushiki Kaisha, Tokyo, Japan

[21] Appl. No.: 62,579

[22] Filed: Jun. 16, 1987

[51] Int. Cl.$^4$ .............................................. G01N 33/48
[52] U.S. Cl. .................................... 436/63; 436/172
[58] Field of Search ....................... 435/39, 40, 808, 6; 436/63, 94, 163, 164, 177, 172, 86, 175; 250/461.2, 461.1, 372, 373, 459.1

[56] References Cited

U.S. PATENT DOCUMENTS

| | | | |
|---|---|---|---|
| 3,566,114 | 2/1971 | Brewer | 250/461.2 |
| 4,503,149 | 3/1985 | Boyd | 250/461.2 |
| 4,686,372 | 8/1987 | Satoru et al. | 250/461.2 |

FOREIGN PATENT DOCUMENTS

WO45544  11/1984  Japan .
59-205998  11/1984  Japan .

Primary Examiner—Barry S. Richman
Assistant Examiner—T. J. Wallen
Attorney, Agent, or Firm—Bernard, Rothwell & Brown

[57] ABSTRACT

In the method for measuring cell counts or methane producing activity of Methanogens according the present invention, an extracted liquid is prepared by adding an addition solution for extracting a particular fluorescent substance inherent to Methanogens, for example, F$_{420}$ exciting in the energy metabolism system of Methanogens in the object for examination and functioning as the electron carrier in the electron transport system or by heating the first object for examination. Since a particular fluorescent substance existing in the Methanogen cells in the first object for examination has been extracted out of the Methanogen cells, the intensity of fluorescence is increased upon measurement thereof. The particular fluorescent substance extracted from the inside to the outside of the Methanogen cells and water soluble substances already existing in the Methanogen cells are contained in the extracted and separated liquid obtained by applying solid-liquid separating procedures of removing solid particles greater than a predetermined grain size containing Methanogens from the extracted liquid. Then, the solid-liquid separating procedure is applied to the second object for examination containing the same ingredients as in the first object for examination and Methanogens, thereby obtaining a solid-liquid separated liquid containing water-soluble substance out of the cells prepared by removing solid particles greater than a predetermined particle size containing Methanogens. By applying an extracting procedure by the addition of an addition solution or heat to the solid-liquid separation, separated and extracted liquid is obtained. Since Methanogens have been previously removed from the separated and extracted liquid, by the solid-liquid separation, no substantial particular fluorescent substance is extracted if subsequent extraction is applied. Then, when an excitation light at a particular wavelength is irradiated to both of the extracted and separated liquid and the separated and extracted liquid, since fluorescent lights of particular wavelength regions are respectively radiated from both of the liquids, the intensity of the fluorescence in each of the particular wavelength region is measured. Then, the cell counts or methane producing activity of Methanogens in the object for examination prepared by sampling the first and second objects for examination are determined by performing predetermined data processing based on the measured intensity value of the fluorescence, since the measured intensity values of the fluorescence have a predetermined relationship with the amount of the particular fluorescent substance that has been present in Methanogen cells.

32 Claims, 8 Drawing Sheets

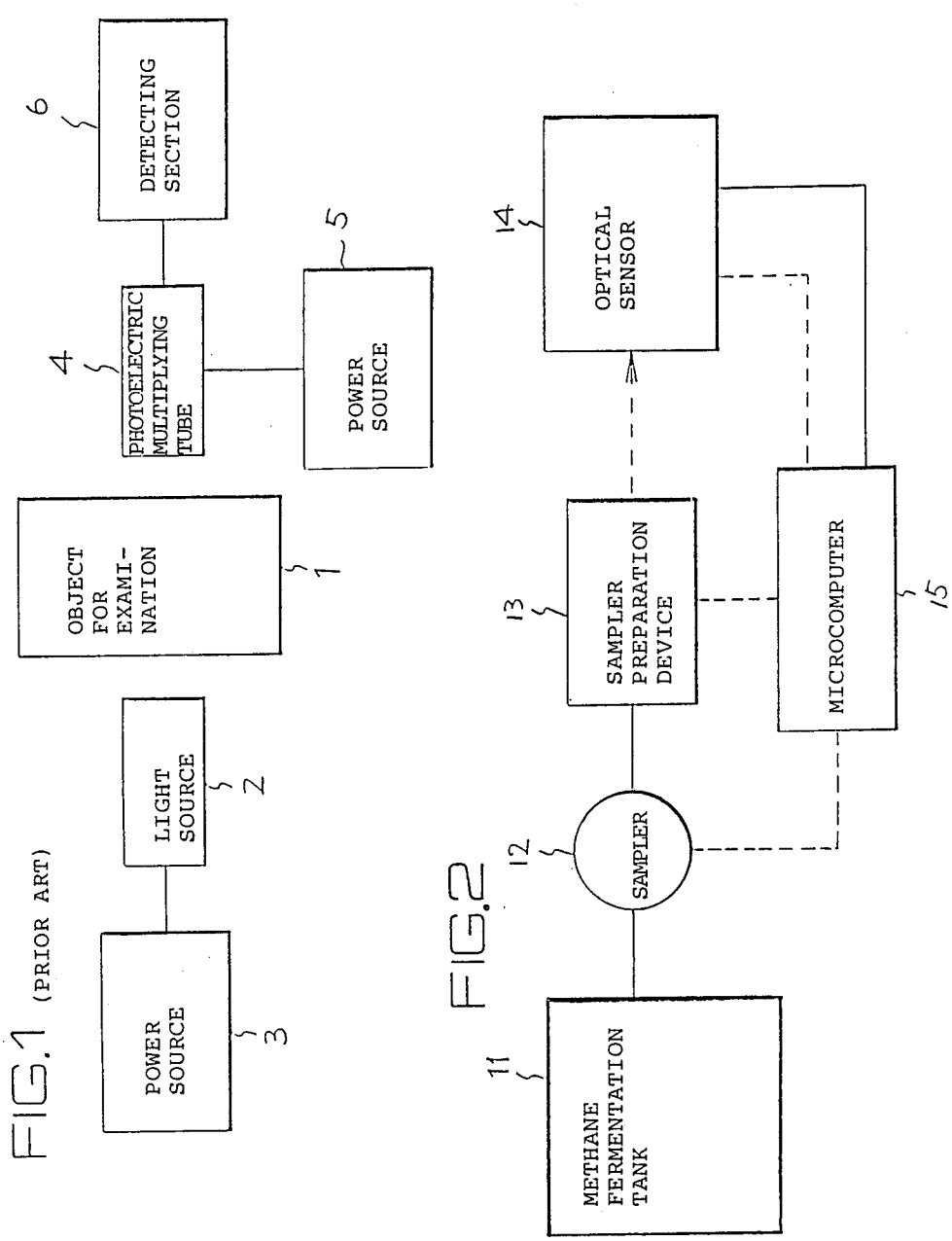

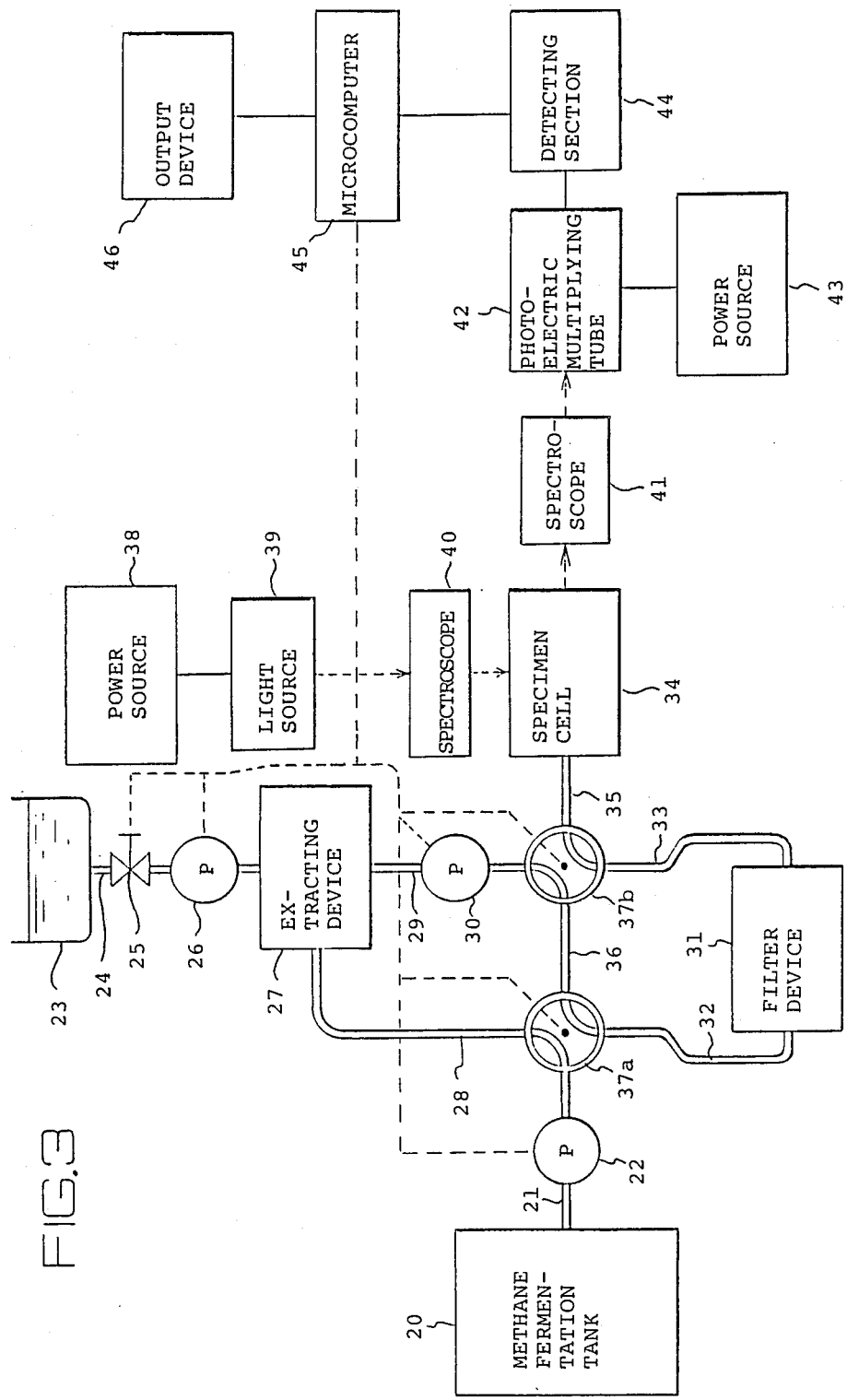

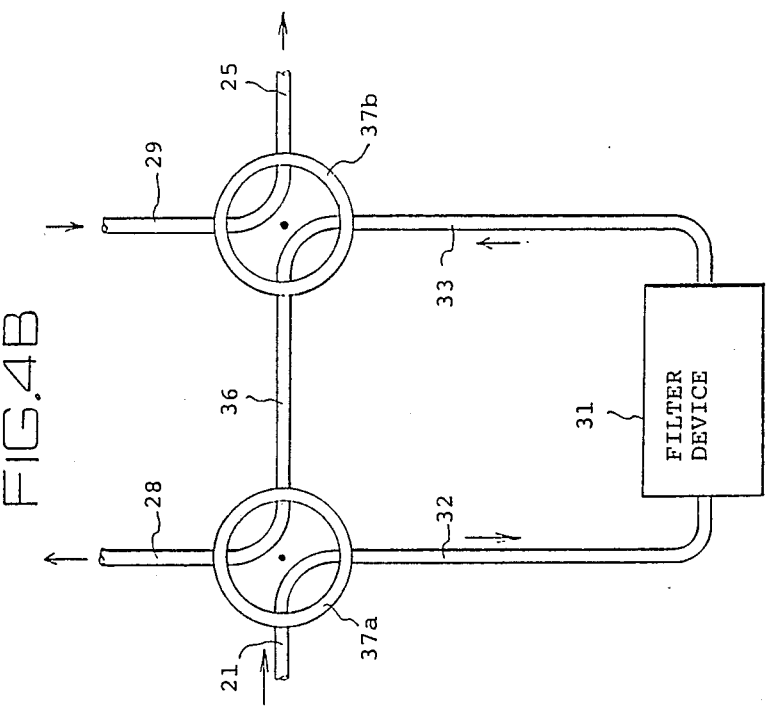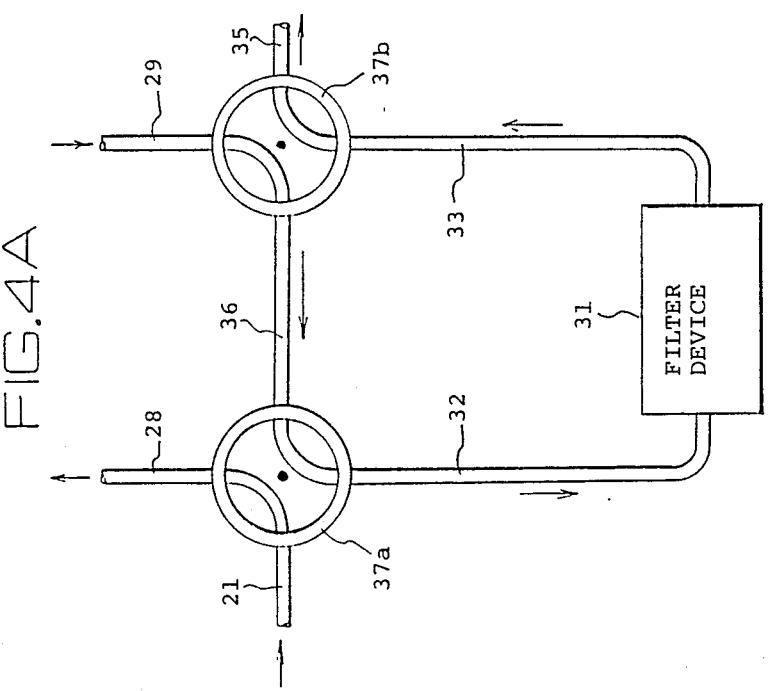

FLUORESCENCE INTENSITY (OPTIONAL UNIT)
EXCITATION LIGHT WAVELENGTH : 420 nm
FLUORESCENCE WAVELENGTH : 470 nm y-axis: METHANOGEN COUNT ($\times 10^8$ CELLS/ml)

FLUORESCENCE INTENSITY (OPTIONAL UNIT)
EXCITATION LIGHT WAVELENGTH : 420 nm
FLUORESCENCE WAVELENGTH : 470 nm y-axis: METHANE GENERATION AMOUNT (OPTIONAL UNIT)

METHOD FOR MEASURING CELL COUNTS AND/OR METHANE PRODUCING ACTIVITY OF METHANOGENS

BACKGROUND OF THE INVENTION

1. Field of the Invention

This invention relates to a method for measuring cell counts and/or methane producing activity of Methanogens in a Methanogens containing sample and, more particularly, it concerns a method which is applicable to the measurement of cell counts and/or methane producing activity of Methanogens existing in a multitude of microorganism groups and foreign substances such as digested sludge, for example, in a methane fermentation tank of a sewage treatment system.

2. Description of the Prior Art

FIG. 1 is a conceptional view, for example, of a modification based on a device for measuring the concentration of microorganism shown in ("Methodology for Microbiological Experiment", 206p, 1975, edited by Tomomichi Yanagida, published from Kodansha). In the figure, are shown an object for examination containing microorganisms, a light source 2, a power source 3 for applying a voltage to the light source 2, a photoelectric multiplying tube 4 opposed to the light source 2 by way of the object for examination 1, a power source 5 for applying a voltage to the photoelectric multiplying tube 4 and a detecting section for measuring the photocurrent from the electric multiplying tube 4.

In the following, explanations will be given as to a conventional method of measurement. Light emitted from the light source 2 transmits through the object for examination 1 containing microorganisms and the transmitted light is received by the photoelectric multiplying tube 4 and its intensity is measured by the detecting section 6 as a photocurrent value from the photoelectric multiplying tube 4. Since there is established a definite relationship between the absorbance and the concentration of microorganisms existing in the object for examination 1 when a visible light is used as the light source, the concentration of microorganism can be evaluated by measuring the absorbance as a result of or in connection with which, the cell counts or microbial activity can be evaluated.

Also, as another method for measuring the microbial activity, there has been a method of optically measuring a quantity of a biological substance related to the energy metabolism which is called "ATP" (Adenosine triphosphate) or "NAD(P)H" [Nicotinamide adenine Dinucleotide (phosphate)] contained in microorganisms.

As mentioned above, since the conventional method for measuring the cell counts or the activity of microorganism is to measure the absorbance of an object for examination, such method is effective so far as the object for examination is composed of only one kind of microorganism and no foreign substances such as sludge, etc. are contained in the object for examination. However, in the case where the object for examination is composed of various kinds of microorganisms and, moreover, foreign substances are contained therein, for example, as an object for examination in a methane fermentation tank where light is absorbed and scattered by and fluorescence is emitted from the substances, it was impossible to selectively measure the cell counts or the activity of a particular kind of microorganism which is desired to be measured. Further, since ATP and NAD(P)H are biological substances existing in all kinds of microorganisms, the method is not suitable for measuring the cell counts or the methane producing activity of Methanogens alone, and it results in a difficulty for continuously distinguishing ATP and NAD(P)H dissolved in the outside of the cells of microorganisms and other dissolved substances from ATP and NAD(P)H within the cells of the microorganisms.

One example of the prior art is disclosed as U.S. Ser. No. 694,384 (Japanese laid-open No. Sho 59-205998).

SUMMARY OF THE INVENTION

The present invention has been achieved for overcoming the foregoing problems and it is an object thereof to obtain a method for measuring cell counts and/or the methane producing activity of Methanogens capable of measuring the cell counts and/or the methane producing activity of the Methanogens at high accuracy and high sensitivity even when a sample to be analyzed contains many kinds of microorganisms, foreign substances and Methanogens is used.

The method for measuring cell counts and/or methane producing activity of Methanogens according the present invention comprises conducting a first extraction by mixing an addition solution with a first fraction of a Methanogens-containing sample to extract from the Methanogen cells a particular fluorescent substance inherent to and contained in the Methanogen cells to obtain an extracted liquid, applying a solid-liquid separating procedure for removing solid particles of greater than a predetermined particle size containing Methanogen from the extracted liquid thereby obtaining an extracted and separated liquid containing the particular fluorescent substance, irradiating an excitation light in a first particular wavelength region to the extracted and separated liquid thereby measuring the intensity of the fluorescence in a second particular wavelength region emitted from the extracted and separated liquid thereby obtaining a first measured value, applying a solid-liquid separating procedure to a second fraction of the Methanogen-containing sample thereby obtaining a solid-liquid separated liquid, mixing the same kind of addition solution as the previous addition solution with the solid-liquid separated liquid thereby obtaining a separated and extracted liquid, irradiating an excitation light in the first particular wavelength region to the separated and extracted liquid thereby measuring the intensity of the fluorescence in the second particular wavelength region radiated from the separated and extracted liquid thereby obtaining a second measured value, and performing a predetermined data processing based on said first and second measured values thereby obtaining calculated values for the cell counts and/or methane producing activity of Methanogens.

A method for measuring cell counts and/or methane producing activity of Methanogens according to another aspect of the present invention comprises applying heat to a first fraction of a Methanogen-containing sample thereby extracting from the Methanogen cells a particular fluorescent substance inherent to and contained in the Methanogen cells to obtain an extracted liquid, then applying a solid-liquid separating procedure for removing solid particles greater than a predetermined particle size containing Methanogens from the extracted liquid thereby obtaining an extracted and separated liquid containing the particular fluorescent substance, irradiating an excitation light in a first particular wavelength region to the extracted and separated liquid thereby measuring the intensity of the fluorescence in a second particular wavelength region emitted from the extracted and separated liquid thereby obtaining a first measured value, applying a solid-liquid separating procedure to a second fraction of the Methanogen-containing sample thereby obtaining a solid-liquid separated liquid, applying heat to the solid-liquid separated liquid thereby obtaining a separated and extracted liquid, irradiating an excitation light in first particular wavelength region to the separated and extracted liquid thereby measuring the intensity of the fluorescence in second particular wavelength region emitted from the separated and extracted liquid thereby obtaining a second measured value, and performing a predetermined data processing based on the first and the second measured values; thereby obtaining calculated values for cell counts or methane producing activity of Methanogens in the sample to be analyzed.

BRIEF DESCRIPTION OF THE DRAWINGS

FIG. 1 is a block diagram showing a measuring device for the explanation of the conventional method;

FIG. 2 is a conceptional view of a measuring device for better understanding of one embodiment according to the present invention;

FIG. 3 is a block diagram for the measuring device for the explanation of one embodiment according to the present invention;

FIGS. 4A and 4B are views showing each of the switched states of electrically driven four-way cocks in FIG. 3;

DETAILED DESCRIPTION OF THE PREFERRED EMBODIMENTS

Figure 5:
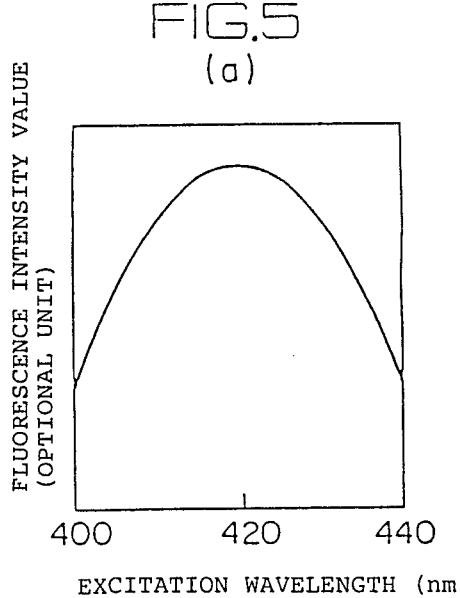
FIGS. 5(a) and 5(b) are diagrams showing the intensity value of fluorescence relative to the wavelength of an excitation light in the first experimental example in accordance with one embodiment of the present invention.
Figure 5:
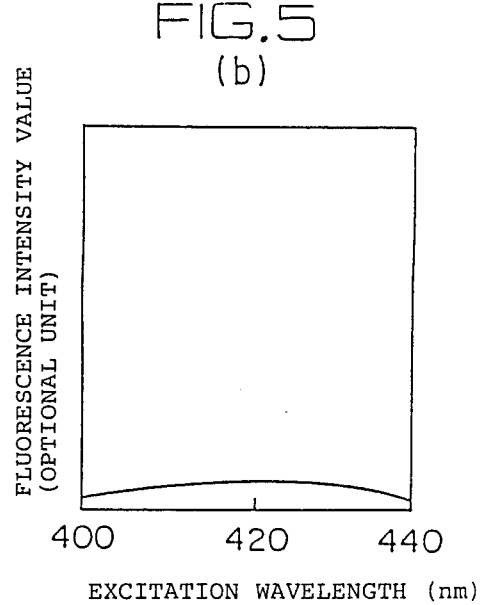

In the following, the present invention will be described by way of its preferred embodiments while referring to the accompanying drawings.

At first, examination will be given as to the principle of the present invention for better understanding of the embodiment according to the present invention. For extracting a particular fluorescent substance characteristic of Methanogens, such as $F_{420}$ that functions as an electron carrier in an electron transport system existing in the energy metabolism system of Methanogens contained in a sample to be analyzed, a liquid additive (and/or heat) is added to a first Methanogen-containing fraction of the sample to be analyzed. The extracted liquid obtained by the extracting treatment increases the intensity of fluorescence upon fluorescence measurement because the particular fluorescent substance existing so far in the Methanogens in the first fraction is now extracted out of the Methanogen cells. Solid-liquid separation is applied by filtering the extracted liquid by way of filtration (or further applying other solid-liquid separating procedure) thereby obtaining an extracted/separated liquid containing Methanogens, with solid particles greater than a predetermined particle size removed. This extracted and separated liquid contains the particular fluorescent substance extracted from the Methanogen cells, as well as extracellular water-soluble substances. A second Methanogens-containing fraction of the sample to be analyzed is filtered (or subjected to another solid-liquid separating procedure). This procedure yields a solid-liquid separated liquid containing Methanogens as well as extracellular water-soluble substances from the second fraction, with solid particles greater than a predetermined particle size removed. The liquid additive as described above (and/or heating) is applied to the solid-liquid separated liquid to obtain a separated/extracted liquid. When an excitation light at a specific wavelength region is applied to both of the extracted/separated liquid and separated/extracted liquid, fluorescent lights of particular wavelength regions are emitted respectively from both of the liquids. The intensity of fluorescence in each of the particular wavelength regions is measured. Since the measured intensity value for each fluorescent light has a predetermined relationship (for example, a proportional relationship) with the quantity of a particular fluorescent substance in the Methanogen cells and also has a predetermined relationship with the cell counts and/or methane producing activity of the Methanogens, the cell counts and/or the methane producing activity of Methanogens in the object for examination sampled from the first and the second fractions can be measured by applying a predetermined data processing based on the measured intensity values of fluorescence. By the way, it has been known that Methanogen has physiological properties different from those of ordinary microorganisms but specific to it, although its electron transport system which takes part in the energy metabolism of Methanogens has not yet been clarified in its entirety. It has already been known that, in this electron transport system existing in the energy metabolism system of the Methanogens, a substance called "$F_{420}$" functions as the electron carrier, which is the substance characteristic of to Methanogens and does not exist in other biological bodies. Therefore, if the substance mainly composed of $F_{420}$ and taking part in the electron transport system of Methanogens processes its physiochemical properties which are peculiar to it and measurable and are different from those of the microorganism groups other than the Methanogen and foreign substances in the object for estimation such as digested sludge, etc. and if it is measurable in the state of viable cells (i.e., microorganisms in the living state), such a substance can be used as a parameter in measuring the cell counts and/or the methane producing activity of Methanogens. In particular, since particular fluorescent substance mainly composed of $F_{420}$, which takes part in the electron transport system of Methanogens is directly related to the methane producing mechanism in its physiological function, it can be an effective object in the measurement of the methane producing activity.

Before showing examples, a concept for one embodiment will be explained referring to FIG. 2 for better understanding of the example according to the present invention. In FIG. 2, 11 denotes a methane fermentation tank containing a sample to be analyzed which contains Methanogens, 12 represents a sampler such as a pump for sampling from the methane fermentation tank, 13 represents a sampler preparation device for applying to the fraction sampled by the sampler 12 an extracting treatment for extracting a particular fluorescent substance out of the Methanogen cells and applying a solid-liquid separating treatment for removing solid particles greater than a predetermined particle size containing Methanogens, 14 represents an optical sensor for measuring the intensity of the fluorescence of the extracted and separated liquid produced in the sampler preparation device 13, and 15 represents a microcomputer for controlling the sampler preparation device 13 and the optical sensor 14, as well as for processing signals detected by the optical sensor 14.

Explanation will now be made of the operation. The sample to be analyzed from the methane fermentation tank 11 by the operation of the sampler 12 is at first applied with the extracting treatment in the sampler preparation device 13 in accordance with the instruction from the microcomputer 15 and then applied with the solid-liquid separating treatment in the sampler preparation device 13. The thus obtained extracted and separated liquid is irradiated with an excitation light and the intensity of a fluorescence thereof is measured by the optical sensor 14. Then, the a second fraction of the sample to be analyzed is subjected to a solid-liquid separating treatment in the sampler preparation device 13 in accordance with the instruction from the microcomputer 15 and then applied with the extracting treatment in the same manner. The thus obtained separated and extracted liquid is irradiated with an excitation light and the intensity of the fluorescence thereof is measured by the optical sensor 14. The difference between two fluorescence signals obtained as described above is calculated by the microcomputer 15 and the cell counts and methane producing activity of Methanogens in the sample are determined based on the calculated value.

FIG. 3 is a block diagram for the device for measuring cell counts or methane producing activity of Methanogens applied with one embodiment according to the present invention. In the figure, are shown a methane fermentation tank 20 which contains Methanogens, a first pipe 21 for taking out the sample to be analyzed from the methane fermentation tank 20, a first liquid supplying pump 22 disposed midway of the first pipe 21, a liquid reservoir 23 containing an addition liquid, for example, an aqueous NaOH solution for extracting a particular fluorescent substance (for example, $F_{420}$) out of the Methanogen cells, a second pipe 24 connected to the bottom of the liquid reservoir 23 for sending the addition solution, a solenoid valve 25 for the ON-OFF control of the flow channel of the second pipe 24, a second liquid supply pump 26 disposed midway of the second pipe 24, an extracting device 27 for applying extracting treatment, to which are supplied the addition solution in the reservoir 23 which enters through the second pipe 24 and the sample to be analyzed from the methane fermentation tank 20 or the liquid prepared from the sample to be analyzed by the solid-liquid separating treatment by the filtration in a filter device 31 described later, and both of the liquids flowing from the second and third pipes 24 and 28 are mixed and applied with the extracting treatment. There are also shown a fourth pipe 29 for delivering the extracted liquid applied with the extracting treatment in the extracting device 27 from the device 27, a third liquid supply pump 30 disposed at the midway of the fourth pipe 29, a filtering device 31 for applying solid-liquid separating treatment to remove solid particles greater than a predetermined particle size containing Methanogen from the extracted liquid, a fifth pipe 32 used for introducing sample to be analyzed from the methane fermentation tank 20 or the extracted liquid prepared by extracting the sample in the extracting device 27 to the inside of the filtering device 31, a sixth pipe 33 for delivering the liquid subjected to solid-liquid separating treatment in the filtering device 31 therefrom, a specimen cell 34 for containing the extracted and separated liquid prepared by applying the extracting treatment to the sample from the methane fermentation tank 20 in the extracting device 27 followed by the solid-liquid separating treatment in the filtration device 31 for measurement, or containing the separated and extracted liquid prepared by applying solid-liquid separating treatment to the sample from the methane fermentation tank 20 in the filtering device 31, followed by the extracting treatment in the extraction device 27 for measurement, a seventh pipe 35 in communication with the specimen cell 34 for introducing the extracted and separated liquid or separated and extracted liquid into the specimen cell 34, a relay pipe 36 for relaying the pipes, a first electrically driven four-way cock 37a that takes a first cock state in which the flow channels in the first and third pipes 21 and 28 are connected with each other and the flow channels in the fifth pipe 32 and the relaying pipe 36 are connected with each other, or a second cock state in which the flow channels in the first and the fifth pipes 21 and 32 are communicated with each other and the flow channels in the third pipe 28 and the relay pipe 36 are connected with each other, a second electrically driven four-way cock 37b which is switched interlocked with the first electrically driven four-way cock 37a and takes, upon switching of the cock, a third cock state in which the flow channels in the fourth pipe 29 and the relay pipe 36 are connected with each other and the flow channels in the sixth and seventh pipes 33 and 35 are connected with each other, or a fourth cock state in which the flow channels in the fourth and seventh pipes 29 and 35 are connected with each other and the flow channels of the sixth pipe 33 and the relay pipe 36 are connected with each other, a power source 38 for light source, a light source 39 connected to the power source 38, a first spectroscope 40 for entering an excitation light to the inside of the specimen cell 34 by restricting the wavelength region of the light from the light source 39, a second spectroscope 41 for transmitting the fluorescence emitting from the measuring liquid in the specimen cell 34 while restricting the wavelength region for the fluorescence upon entrance of the excitation light from the light source 39, a photoelectric multiplying tube 42 for receiving the fluorescence of a specific wavelength region transmitted through the second spectroscope 41, a power source 43 for the photoelectric multiplying tube 42, a detecting section 44 for detecting the photocurrent from the photoelectric multiplying tube 42, a microcomputer 45 having a memory function for storing the measured intensity signals for the fluorescence detected in the detecting section 44 while converting them from analog into digital form, calculating function, etc. and controlling the driving for the first through third pumps 22, 26 and 30, ON-OFF operation for the solenoid valve 25, cock switching for the first and second electrically driven four-way cocks 37a and 37b, as well as the first spectroscope 40, and an output device 46 such as a printer or CRT for outputting the result of measurement processed in the microcomputer 45.

FIGS. 4A and 4B are views illustrating each of the cock switched states of the first and the second electrically driven four-way cocks 37A and 37B. In FIG. 4A, the first electrically driven four-way cock 37A is in the first cock state and the second electrically driven 4-way cock 37B is in the third cock state as described above. In FIG. 4B, the first electrically driven 4-way cock 37a is in the second state and the second electrically driven four-way cock 37b is in the fourth cock state.

Explanation will then be made of now operation of such a device. As shown in FIG. 4A, the first electrically driven four-way cock 37a is set to the first cock state and the second electrically driven four-way cock 37b is set to the third cock state as described above under the control of the microcomputer 45.

The sample from the methane fermentation tank 20 is introduced in a predetermined amount to the inside of the extracting device 27 along the flow channel of the first pipe 21 by way of the first pump 22→the first electrically driven four-way cock 37a→the third pipe 28 by the operation of the first pump 22. Further, the addition solution in the liquid reservoir 23 is introduced in a predetermined amount to the inside of the extracting device 27 along the flow channel of the second pipe 24 by the opening operation of the solenoid valve 25 for a certain period of time and the actuation of the second pump 26. Then, the sample and the addition solution are mixed in the extracting device 27 to thereby obtain an extracted liquid in which a particular fluorescent substance in the inside of Methanogens contained in the object for examination is extracted out of the cell body. The extracted liquid is introduced from the extracting device 27 to the inside of the filtering device 31 along the flow channel of the fourth pipe 29 by way of the third pump 40→second electrical driven four-way cock 37b→the relaying pipe 36→the first electrically driven four-way cock 37a→the fifth pipe 32 by the operation of the third pump 30. The extracted liquid introduced to the inside of the filtering device 31 is applied with the solid-liquid separating treatment for separating solid particles greater than a predetermined particle size containing Methanogens in the filtering device 31, and the extracted and separated liquid obtained through the solid-liquid separating treatment is sent from the filtering device 31 along the flow channel of the sixth pipe 33→the second electrically driven four-way cock 37b→the seventh pipe 35 and contained in the specimen cell 34. The light from the light source 39 driven from the power source 38 is restricted to a certain wavelength region by the first spectroscope 40 controlled by the microcomputer 45 so as to allow the light only for a specific wavelength region to transmit therethrough and irradiated as an excitation light to the extracted and separated liquid in the specimen cell 34. Upon irradiation by the excitation light, the extracted particular fluorescent substance in the extracted and separated liquid is excited to emit a fluorescence. The fluorescence is restricted to a particular wavelength region upon passing through the spectroscope 41 and then enters into the photoelectric multiplying tube 42. A photocurrent is generated in accordance with the intensity of the fluorescence entering the photoelectric multiplying tube 42 and it is detected by the detection section 44. The detection signal is inputted and stored in the microcomputer 45. In this way, the microcomputer 45 controls the first spectroscope 40 to successively vary the wavelength region of the excitation light entering to the inside of the specimen cell 34 and measured the intensity of the fluorescence successively, whereby an intensity distribution for the fluorescence relative to the wavelength of the excitation light can be obtained. After the measurement, the extracted and separated liquid in the specimen cell 34 is discharged externally.

Then, the first and the second electrically driven four-way cocks 37a and 37b are switched from the state shown in FIG. 4A to the state shown in FIG. 4B under the control of the microcomputer 45. That is, the first electrically driven cock 37a is set to the second cock state, while the second electrically cock 37b is set to the fourth cock state. By the operation of the first pump 22, the sample from the methane fermentation tank 20 is introduced through along the first pipe by way of the first pump 22→the first electrically driven four-way cock 37a→the fifth pipe 32 and introduced to the inside of the filtering device 31. The separated liquid obtained by apply the solid-liquid separating treatment to the sample to be analyzed in the filtering device 31 is introduced from the filtering device 31 along the flow channel of the sixth pipe 33→the second electrically driven four-way cock 37b→relay pipe 36→the first electrically driven four-way cock 37a→the third pipe 28 and introduced into the extracting device 27. After the introduction, the addition solution in the liquid reservoir 23 is introduced in a predetermined amount into the extracting device 27 by the opening operation of the solenoid valve 25 for a predetermined of time and the actuation of the pump 26, and mixed with the liquid applied with the solid-liquid separation treatment as the filtered liquid to conduct the extracting treatment. The separated and extracted liquid obtained by the extracting treatment is sent by the actuation of the pump 30 along the flow channel of the fourth pipe 29 by way of the third pump 30→the second electrically driven four-way cock 37b→the seventh pipe 35 and contained in the specimen cell 34. The intensity of the fluorescence of the separated and extracted liquid in the specimen cell 34 is measured successively while varying the wavelength region of the excitation light in the same manner as for the measurement of the intensity of the fluorescence by using the extracted and separated liquid as described above, and the result of each measurement is stored into the microcomputer 45. Then, the microcomputer 45 obtains the cell counts or the methane producing activity of Methanogens, by calculation or the like, based on the value obtained by subtracting the result of measurement of the intensity of the fluorescence obtained upon using the separated and extracted liquid from the result of measurement for the fluorescent light intensity obtained upon using the extracted and separated liquid and outputs the value by way of an output device 46. Upon conducting the above-mentioned operation, the microcomputer 45 performs control for the actuation and deactuation for the first through third pumps 22, 26 and 30, ON-OFF operation for the solenoid valve 25, cock switching for the first and second electrically driven four-way cocks 27A and 27B and for the first spectroscope 40.

EXPERIMENTAL EXAMPLE (1)

The experimental example shows a case where Methanosarcina barkery as a sort of Methanogen (hereinafter simply referred to as M. barkery) was cultivated batchwise, and the intensity of the fluorescence from the cultivated suspension in the logarithmic phase was measured by using the measuring device shown in FIG. 2. For the measurement of the intensity of the fluorescence, the wavelength of the excitation light for emitting the fluorescence was varied within a wavelength region from 400 to 440 (nm) and the distribution for the intensity of the fluorescence at a wavelength of 470 (nm) was determined in this wavelength region.

Figure 6:
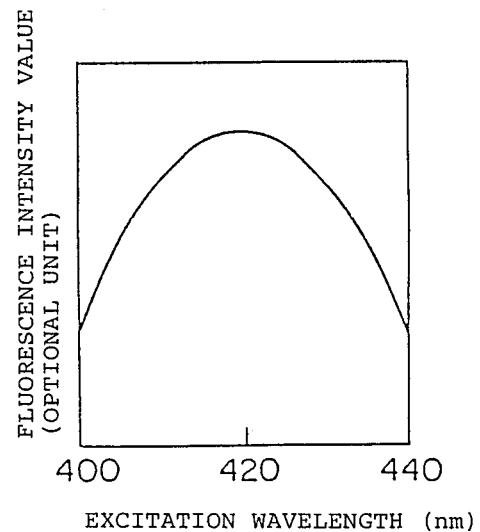
FIG. 6 is a diagram showing the intensity value of the fluorescence relative to the wavelength of the excitation obtained from the data shown in FIGS. 5(a) and 5(b)

Further, filters made of acetyl cellulose having a pore size of 0.22 (um) were used for the filtering device 31, while an aqueous NaOH solution was used as the addition solution in the liquid reservoir 23. FIG. 5(a) shows the distribution of the intensity of the fluorescence in the extracted and separated liquid relative to the wavelength of the excitation light by measurement, FIG. 5(b) shows the distribution of the intensity of the fluorescence in the separated and extracted liquid by measurement relative to the wavelength of the excitation light. FIG. 6 shows the distribution of the intensity of the fluorescence relative to the wavelength of the excitation light based on the data shown in FIGS. 5(a) and 5(b), for which the difference is determined by the microcomputer 45. The intensity value for the fluorescent light in FIG. 5 means the measured value for the intensity of the fluorescence and the intensity value for the fluorescence in FIG. 6 means the intensity value of the fluorescent light obtained from the measured value for the intensity of the fluorescent light, in this and succeeding experimental examples.

In this experimental example, since Methanogens were being grown in the fermentor and almost all of the Methanogens had methane producing activity, it can be seen that $F_{420}$ scarcely leaked to the outside of the Methanogen cells, the difference for the intensity value of the fluorescence shown in FIG. 5 is great and the intensity value for the fluorescence due to $F_{420}$ having been contained in the Methanogen is great as shown in FIG. 6.

Figure 7:
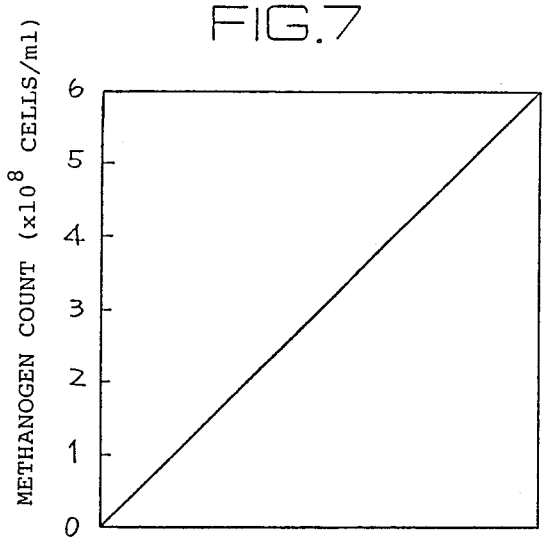
FIG. 7 is a diagram showing a relationship of cell counts of Methanogens relative to the intensity value of the fluorescence.
Figure 8:
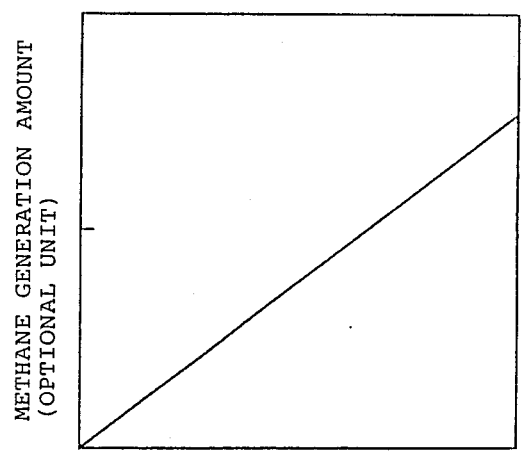
FIG. 8 is a diagram showing a relationship of the amount of methane generated relative to the intensity value of the fluorescence.

Then, FIGS. 7 and 8 show respectively the relationship between the thus measured intensity value for the fluorescence and the cell counts of the Methanogen, as well as the between the intensity value for the fluorescence and the methane producing rate. In each of FIGS. 7 and 8, the abscissa indicates the intensity value for the fluorescence at the wavelength of the fluorescence of 470 nm when the wavelength of the fluorescent light is 420 (nm), while the ordinate indicates the cell counts of Methanogens or the methane producing amount respectively. If the linear calculation formulas shown in FIGS. 7 and 8 are memorized in the microcomputer 45, the cell counts or the methane producing activity of Methanogens can be measured accurately by the measuring device by performing calculation using the calculation formulas and the measured values for the intensity of the measured fluorescence (intensity value of the fluorescence).

EXPERIMENTAL EXAMPLE (2)

Figure 9:
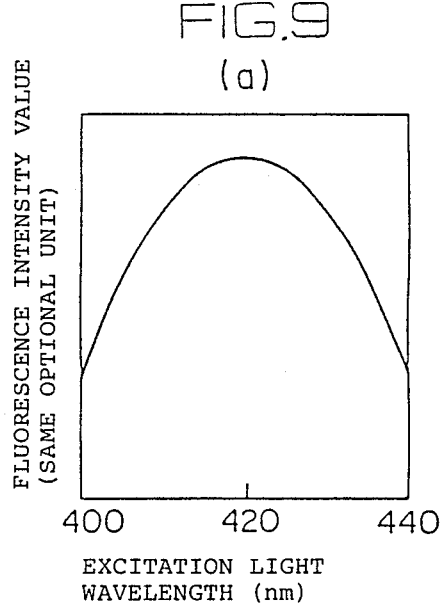
FIGS. 9(a) and 9(b) are diagrams showing the intensity value of the fluorescence relative to the wavelength of an excitation light in the second experimental example in accordance with one embodiment of the present invention.
Figure 9:
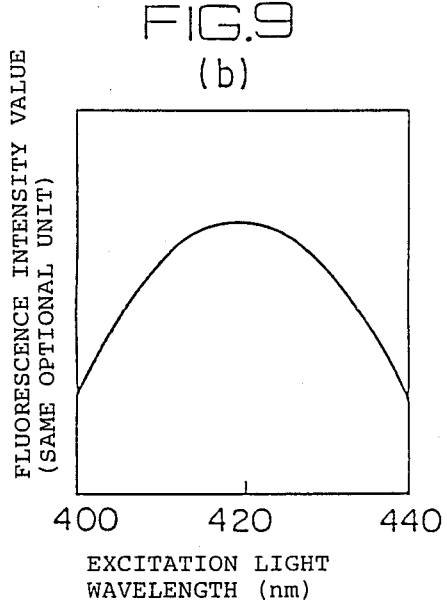
Figure 10:
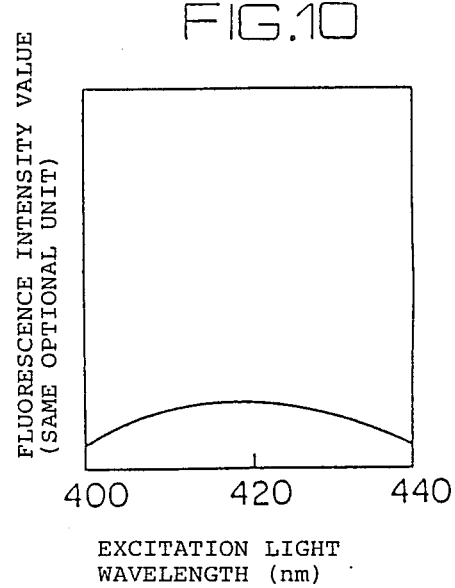
FIG. 10 is a diagram showing the intensity value of the fluorescence relative to the wavelength of the excitation light obtained from the data shown in FIGS. 9(a) and 9(b)

In this experimental example, M. barkery was cultivated batchwise and the intensity of the fluorescence from the cultured suspension in the death phase was measured by using the measuring device shown in FIG. 1. FIGS. 9 and 10 show the result of applying the same treatment as in Experimental Example (1). FIG. 9(a) is a distribution for the intensity of fluorescence from the extracted and separated liquid relative to the wavelength of the excitation light, while FIG. 9(b) shows the distribution for the intensity of fluorescence from the separated and extracted liquid relative to the wavelength of the excitation light. FIG. 10 shows a curve prepared by subtracting the value for the curve in FIG. 9(b) from the value for the curve in FIG. 9(a). Since almost of Methanogens in the sample were dead and $F_{420}$ was leaked out of their cell bodies, the difference of the fluorescence intensity shown between FIGS. 9(a) and (b) was small as shown in FIG. 10 and it can be seen that the methane producing activity is low.

EXPERIMENTAL EXAMPLE (3)

Figure 11:
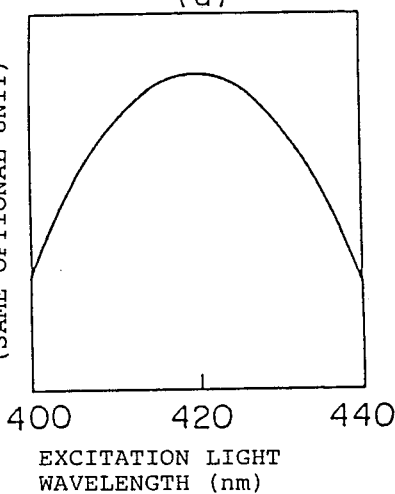
FIGS. 11(a) and 11(b) are diagrams showing the intensity value of the fluorescence relative to the wavelength of an excitation light in the third experimental example in accordance with one embodiment of the present invention.
Figure 11:
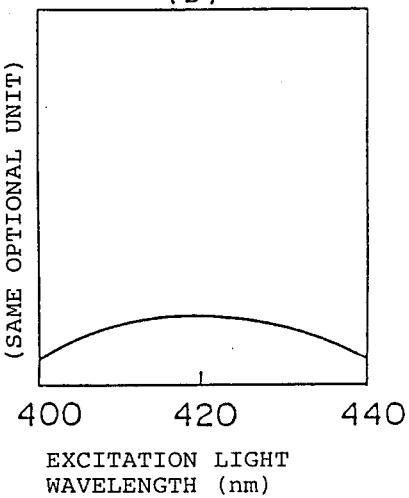
Figure 12:
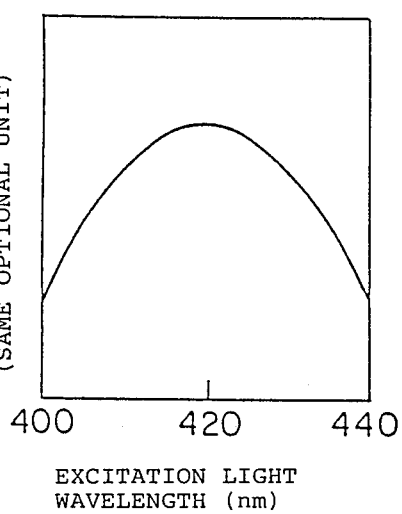
FIG. 12 is a diagram showing the intensity value of the fluorescence relative to the wavelength of an excitation light obtained from the data shown in FIGS. 11(a) and 11(b)
Figure 13:
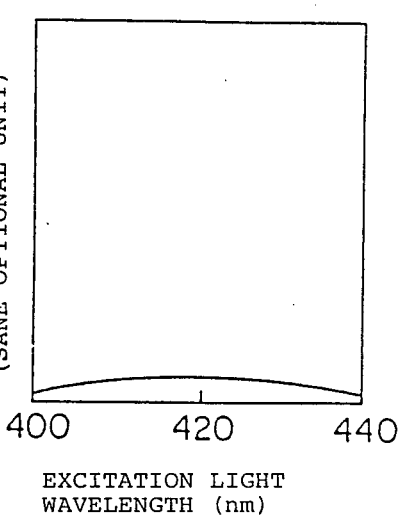
FIG. 13 is a diagram showing the intensity value of the fluorescence relative to the wavelength of an excitation light in the third experimental example in which intensity of the fluorescence is measured without filtering the object for examination; and, FIG. 14 is a block diagram showing another example of a measuring device for the explanation of another embodiment according to the present invention.

In this example, the intensity of the fluorescence from the sludge in the methane fermentation tank of a sewage treating facility was measured by the measuring device in FIG. 2. FIGS. 11 and 12 shows the results of applying the same treatment as in Experimental Example (1). FIG. 11(a) shows the distribution for the intensity of the fluorescence from the extracted and separated liquid, while FIG. 11(b) shows the distribution for the intensity of the fluorescence from the separated and extracted liquid, while FIG. 12 is a curve prepared by subtracting the curve shown in FIG. 11(b) from the curve shown in FIG. 11(a). Since the sludge contained black substances, no substantial fluorescence light was detected if it was not filtered (refer to FIG. 13). However, since the black substances can be removed through the filtration in the measuring device, the intensity of the fluorescence mainly of $F_{420}$ possessed by Methanogens in the sludge could be measured as shown in FIG. 12. It can be seen from the result that the methane producing activity of the methane fermentation sludge from sewage processing facility is high.

While explanation has been made only to M. barkery and the sludge from the sewage processing facility in N city in the foregoing experimental examples, objects for examination are not restricted only to them but Methanogens of other kinds and Methanogens present in other methane fermentation sludges, etc. can also be measured.

In the foregoing examples, the intensity of the fluorescence was measured using the separated and extracted liquid after the intensity of the fluorescence has been measured by using the extracted and separated liquid, but these steps may be reversed in view of a time sequence. Further, the restriction of the particular wavelength region by the first and the second spectroscopes 40 and 41 upon measuring the intensity of the fluorescence in the foregoing examples also means the restriction to the particular wavelength in the above and subsequent examples.

Further, although the intensity distribution of the fluorescence was determined in the foregoing examples, it is also possible to specify the wavelength of the excitation light to a single wavelength (for example, at 420 nm) with no change, determine the measured value for the intensity of the fluorescence by each one in the specified wavelength region, (for example, at 470 nm) from the extracted and separated liquid and the separated and extracted liquid, thereby to obtain a difference between both of the measured values and obtain cell counts or methane producing activity of Methanogens in the sample based on the difference. In this case, the cell counts or methane producing activity of Methanogens in the sample to be analyzed can be obtained, by substituting the difference between both of the measured values as described above into the calculation formula having a relationship as shown in FIG. 7 or 8.

Further, in the foregoing examples, the cell counts or methane producing activity of Methanogens contained in the sample to be analyzed can be obtained, not by determining the difference between the measured intensity values for the fluorescence, but by substituting the measured intensity value of the fluorescence obtained from the extracted and separated liquid (first measured value in the first measuring treatment) into the calculation formula for the relationship shown in FIG. 7 or 8 to obtain the first cell counts or first methane producing activity in the extracted and separated liquid (first calculated value) and then by similarly substituting the measured intensity value of the fluorscence obtained from the separated and extracted liquid (the second measured value in the first measuring treatment) to obtain the second cell counts and the second methane producing activity in the separated and extracted liquid (second calculated value), and by determining the difference between the first and the second cell counts of the Methanogens with each other, or the difference between the first and second methane producing activities with each other. This is also applicable to the subsequent examples, wherein the calculated value can be obtained in this case by preparing the extracted and separated liquid to determine the first calculated value, preparing the separated and extracted liquid to determine the second calculated value and then subtracting the second calculated value from the first calculated value. Also in this case, it is construed that the procedures are included within the data processing based on the first and second calculated values after the first and the second measuring treatments.

Furthermore, although the electrically driven four-way cocks have been used in the foregoing examples for changing the flow channel for the object for examination, extracted treatment, etc., any other method such as the combination of the solenoid valve and three-way tube may be used with no particular restrictions.

Figure 14:
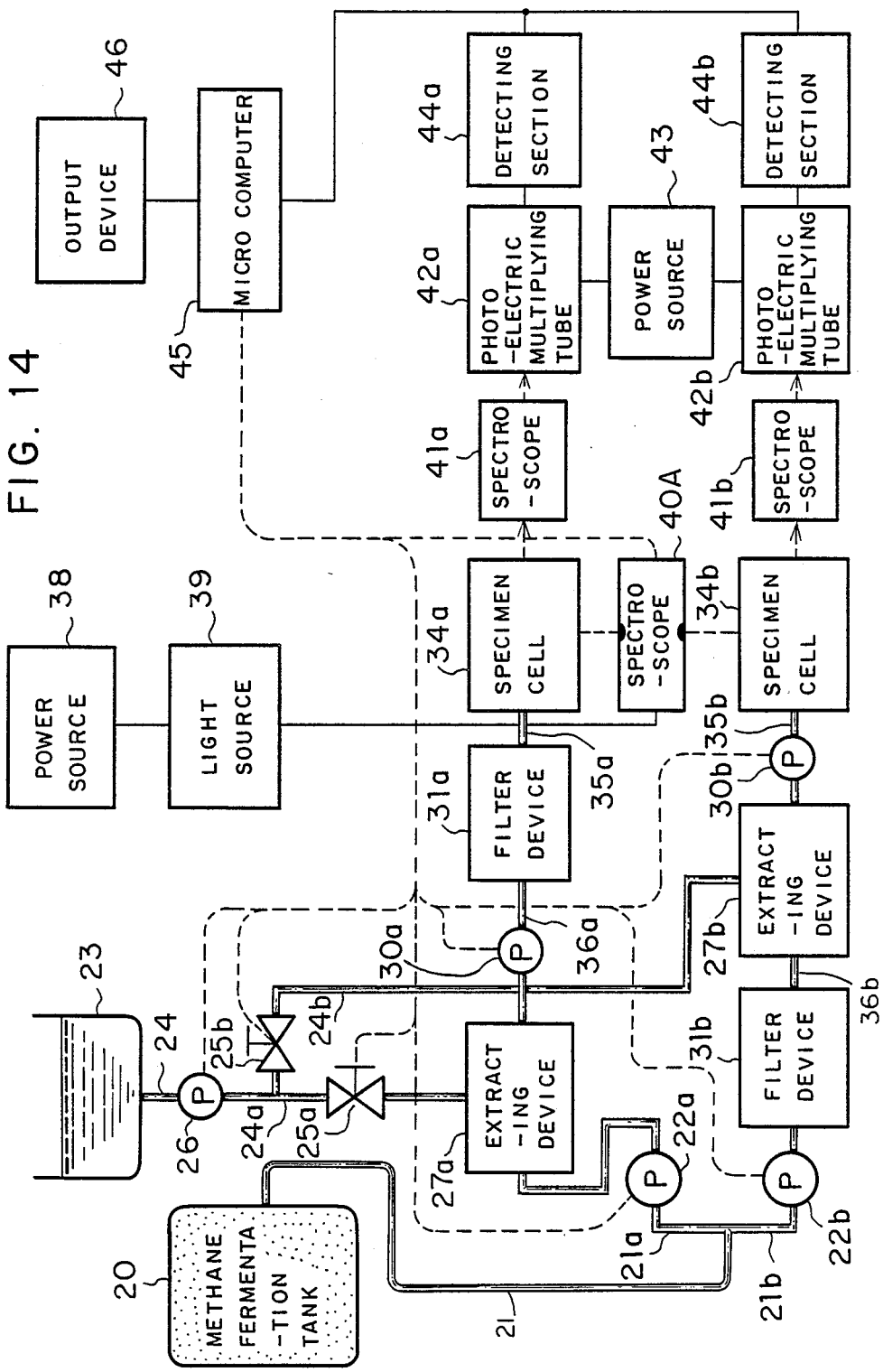

FIG. 14 shows another constituent embodiment of the device for measuring the cell counts or methane producing activity of Methanogens for explaining another embodiment of the present invention, in which an extracted and separated liquid and a separated and extracted liquid are obtained in parallel and the measurement for the intensity of the fluorescence light from both of the liquids is carried out in parallel. In FIG. 14, the portions with identical reference numerals in FIG. 3 are the same as those in FIG. 3, and the portions with identical reference numerals except for their subscripts a and b are the same as those in FIG. 3. A methane fermentation tank 20, first pipe 21, pipe 21a branched from the first pipe 21, pump 22a disposed in the line of the pipe 21a, extracting device 27a, pipe 36a, pump 30a disposed in the line of the pipe 36a, filtering device 31a, pipe 35a and specimen cell 34a are connected in this order. Further, a methane fermentation tank 20, first pipe 21, pipe 21b branched from the first pipe 21, pump 22b disposed in the line of the pipe 21b, filtering device 31b, pipe 36b, extracting device 27b, pipe 35b, pump 30b disposed in the line of the 35b and specimen cell 34b are connected in this order. A liquid reservoir 23 is communicated with the extracting device 27a by way of pipe 24, pump 26 disposed in the line of the pipe 24, pipe 24a branched from the pipe 24 and solenoid valve 25a for the ON-OFF control of the flow channel of the pipe 24b. Further, the liquid reservoir 23 is communicated with the extracting device 27b by way of the pipe 24, pump 26, pipe 24b branched from the pipe 24 and a solenoid valve 25b for the ON-OFF control of the flow channel of the pipe 24b. Reference 40A represents a spectroscope for excitation light, which is adapted to restrict the wavelength region of the light entered from the light source 39 and project an excitation light at the same intensity to the inside of both of the specimen cells 34a and 34b. Spectroscope 41a (41b), photoelectric multiplying tube 42a (42b) connected to a power source 43 and detector 44a (44b) are connected in pair in this order to the specimen cell 34a (34b). The outputs from both of the detectors 44a, 44b are adapted to be inputted to a microcomputer 45. The microcomputer 45 is so adapted that it can control the five pumps 22a, 22b, 26, 30a, 30b, two solenoid valves 25a, 25b and the spectroscope 40A.

A portion of a sample to be analyzed from the methane fermentation tank and a portion of the addition solution in the liquid reservoir 23 are formed into an extracted liquid in the extracting device 27a, further formed into an extracted and separated liquid in the filtering device 31a and then contained in the specimen cell 34a. While on the other hand, another portion of a sample to be analyzed from the methane fermentation tank is formed into a solid-liquid separated liquid in the filtering device 21b, then joined with a portion of the addition solution in the liquid reservoir 23 in the extracting device 27b into a separated and extracted liquid and then contained in the inside of the specimen cell 34b. The excitation light from the light source 39 is irradiated by way of the spectroscope 40A to the extracted and separated liquid in the specimen cell 34a and, at the same time, irradiated to the separated and extracted liquid in the specimen cell 34b. The fluorescence from the extracted and separated liquid and fluorescence from the separated and extracted liquid are measured for the intensity by using each of photoelectric multiplying tubes 42a, 42b, etc. The measured intensity values of the fluorescence are taken into the microcomputer 45 in a time sharing manner and the microcomputer 45 performs a predetermined calculation for determining the cell counts or the methane producing activity of Methanogens in the sample. Although the same result as in the first example can also be obtained in this example, since the processings are performed simultaneously in a parallel manner, the measuring speed is increased as compared with the first example.

While the measured values have been taken into the computer 45 in the time sharing manner, when the computer can perform parallel data processing for a plurality of data, they may be entered and processed in a parallel manner.

In each of the examples, solid-liquid separation is applied by using filters made of organic materials such as acetyl cellulose or cellulose having pore size of 0.22 ($\mu$m), as well as by selectively using: (a) filters made of organic material having a pore since from 0.1 $\mu$m to 1 mm, (b) filters made of inorganic material such as ceramics, (c) centrifugal separator, (d) gel filtration by using gels and (e) dialysis by using dialysis membrane.

As the addition solution for use in the extraction in each of the examples, there can be used, in addition to the aqueous solution of NaOH, any one of the following solutions selectively, such as an organic solvent used alone, a mixed solution of a plurality of kinds of organic solvents at an adequate ratio, a mixed solution of an organic solvent and water, a mixed solution of an organic solvent and an alkaline solution such as an aqueous solution of NaOH, etc. and a mixed solution of a plurality of kinds of alkaline solutions. The organic solvent can include for example, 2-propanol, acetone, ethanol and methanol.

Further, a liquid, for example, to be applied with extraction such as the extracted liquid may be heated upon extraction by providing the extracting device 27, 27a, 27b with a heating function by means of heater or the like, whereby extracting treatment at higher efficiency can be applied.

Further, although the addition solution was applied in each of the examples upon extraction, it is possible to apply the extraction without adding the addition solution to the object for examination or the liquid applied with solid-liquid separation to be applied with the extraction but by merely heating to increase the temperature thereof.

Further, in each of the examples, depending on the kind of sample, the cell counts or methane producing activity of Methanogens can be determined as the value $f(I_{A1}, I_{A2} \ldots$ and $I_{B1}, I_{B2} \ldots)$ or value $f(I_{A1}-I_{B1}, I_{A2}-I_{B2}, \ldots)$ obtained by collectively substituting the measured intensity values for the fluorescence relative to excitation light at a plurality of wavelengths obtained from both of the extracted and separated liquid and separated and extracted liquid (represented as $I_{A1}, I_{A2} \ldots$ and $I_{B1}, I_{B2} \ldots$) into an appropriate calculation formula $f(I)$ [or $f(I_A-I_B)$] and calculating them.

Further, in each of the examples, measured values for the cell counts or methane producing activity of Methanogens can be obtained extremely simply by tabulating the relationship in FIG. 7 or FIG. 8 in the memory of the microcomputer 45 instead of using the calculation formula, and by reference to the table based on the measured intensity values for the fluorescence obtained respectively from the extracted and separated liquid and the separated and the extracted liquid.

Further, in the case of measuring the sample to be analyzed several times within a predetermined period, it is not always necessary to apply solid-liquid separation for each of the cases. For instance, if a value obtained by measuring the intensity of the fluorescence from the extracted liquid obtained by the application of the extracting treatment to the sample to be analyzed after measuring the intensity of the fluorescence both from the extracted and separated liquid and the separated and extracted liquid by the method of the experiment has a certain correlation with the measured intensity value of the fluorescence from the separated and extracted liquid, the cell counts or methane producing activity of Methanogens may be obtained by using the measured intensity value of the fluorescence from the extracted liquid.

Further, depending on the sample to be analyzed, it is possible to measure the cell counts or methane producing activity of Methanogens without applying both of the extraction and the solid-liquid separation but by measuring the intensity of the fluorescence from the sample as it is by merely being diluted with water and using the thus measured value.

According to the present invention as has been described above, extraction is applied to a Methanogens-containing sample by adding an addition solution and-/or increasing the temperature of the sample to prepare an extracted liquid into which a particular fluorescence substance in the Methanogen is extracted, a solid-liquid separating procedure is applied for separating to remove solid particles greater than a predetermined particle size containing Methanogen from the extracted liquid to form an extracted and separated liquid, while the Methanogens-containing sample is subjected to a solid-liquid separation to obtain a solid-liquid separated liquid, the solid-liquid separated liquid is applied with the same extraction as described above to form a separated and extracted liquid, an excitation light in a specific wavelength region is irradiated to the extracted and separated liquid and the separated and the extracted liquid to measure the intensity of the fluorescence in a specific wavelength region radiated respectively from the extracted and separated liquid and the separated and extracted liquid, and a predetermined data processing is performed based on both of the thus obtained measured values to thereby measure the cell counts or methane producing activity of the Methanogens, and it is therefore possible to measure the cell counts or methane producing activity of the Methanogens at a high measuring sensitivity and, particularly, it is possible to measure the cell counts or methane producing activity of Methanogens even from mixed system microorganisms containing foreign substances such as digested sludge in a methane fermertation tank or the like.

What is claimed is:

1. A method for measuring viability of Methanogens which comprises a first treatment, which comprises conducting a first extraction by mixing an addition solution with a first Methanogens-containing sample to extract from the Methanogens, a particular fluorescent substance inherent to and contained in said Methanogens, thereby obtaining an extracted liquid, a first separation of applying a solid-liquid separating procedure for removing solid particles of greater than a predetermined particle size containing Methanogens from the extracted liquid thereby obtaining an extracted and separated liquid containing said particular fluorescent substance, a first measurement of irradiating an excitation light in a particular wavelength region to said extracted and separated liquid thereby measuring fluorescence intensity in a second particular wavelength region radiated from said extracted and separated liquid, thereby obtaining a first measured value, and a second treatment comprising a second separation of applying said solid-liquid separating procedure to a second fraction of the Methanogen-containing sample, thereby obtaining a solid-liquid separated liquid, a second extraction of mixing said addition solution to said solid-liquid separated liquid, thereby producing a separated and extracted liquid, measuring fluorescence intensity in a second particular wavelenqth region radiated from said separated and extracted liquid thereby obtaining a second measured value and performing a predetermined data processing based on said first and second measured values thereby obtaining a calculated value for the viability of Methanogens.

2. A method for mesuring viability of Methanogens as defined in claim 1, wherein the sample and addition solution are heated in the first extraction and the sample and addition solution are heated in the second extraction thereby promoting the extraction.

3. A method for measuring viability of Methanogens as defined in claim 1, wherein the second separation is conducted subsequent to the first measurement.

4. A method for measuring viability of Methanogens as defined in claim 1, wherein the first extraction is conducted subsequent to the second measurement.

5. A method for measuring viability of Methanogens as defined in claim 1, wherein the first treatment from the first extraction to the first measurement and the second treatment from the second separation to the second measurement are carried out in parallel.

6. A method for measuring viability of Methanogens as defined in claim 1, wherein a single organic solvent is used as the addition solution.

7. A method for measuring viability of Methanogens as defined in claim 6, wherein said organic solvent is 2-propanol, acetone, ethanol or methanol.

8. A method for measuring viability of Methanogens as defined in claim 1, wherein a mixed solution of a plurality of kinds of organic solvents is used as the addition solution.

9. A method for measuring viability of Methanogens as defined in claim 1, wherein a mixed solution of a single organic solvent and water is used as the addition solution.

10. A method for measuring viability of Methanogens as defined in claim 1, wherein a mixed solution of a plurality of kinds of organic solvents and water are used as the addition solution.

11. A method for measuring viability of Methanogens as defined in claim 1, wherein a mixed solution of an organic solvent and an alkaline liquid is used as the addition solution.

12. A method for measuring viability of Methanogens as defined in claim 11, wherein an aqueous NaOH solution is used as the alkaline liquid.

13. A method for measuring viability of Methaogens as defined in claim 1, wherein a single alkaline liquid is used as the addition solution.

14. A method for measuring viability of Methanogens as defined in claim 13, wherein an aqueous NaOH solution is used as the alkaline liquid.

15. A method for measuring viability of Methanogens as defined in claim 1, wherein a mixed liquid of a plurality of kinds of alkaline liquids is used as the addition solution.

16. A method for measuring viability of Methanogens as defined in claim 15, wherein an aqueous NaOH solution is included as the alkaline liquids.

17. A method for measuring viability of Methanogens as defined in claim 1, wherein filtration is applied as the solid-liquid separating procedure.

18. A method for measuring viability of Methanogens as defined in claim 1, wherein centrifugal separation as the solid-liquid separating procedure.

19. A method for measuring viability of Methanogens as defined in claim 1, wherein dialysis is applied as the solid-liquid separating procedure.

20. A method for measuring viability of Methanogens as defined in claim 1, wherein the first and second measured values are obtaining by using an excitation light of a single wavelength as the excitation light in the first particular wavelength region in the first and the second measurements, and said first and second measured values are substituted into calculation formulas containing predetermined measured values for the intensity of the fluorescence as the variant, thereby obtaining calculated values in the data processing.

21. A method for measuring viability of Methanogens as defined in claim 1, wherein the first and second measured values each in plurality are obtained by using excitation lights of a plurality of wavelenghts individually as the excitation light in the first wavelength region in the first and the second measurements, and said first and second measured values each in plurality are substituted into calculation formulas containing predetermined measured values for the intensity of each fluorescence relative to each of the wavelengths for said excitation light as the variant, thereby obtaining calculated values in the data processing.

22. A method as defined in claim 1, wherein said viability measurement comprises measuring cell counts of Methanogens.

23. A method as defined in claim 1, wherein said viability measurement comprises measuring methane producing activity of Methanogens.

24. A method for measuring viability of Methanogens which comprises a first treatment, which comprises conducting a first extraction, applying heat to a first Methanogens-containing fraction of a sample to be analyzed thereby extracting out of said Methanogens a particular fluorescent substance inherent to and contained in said Methanogens to obtain an extracted liquid, a first separation of applying a solid-liquid separating procedure for removing solid particles greater than a predetermined particle size containing Methanogens from said extracted liquid containing said particlular fluorescent substance thereby obtaining an extracted and separated liquid containing said particular fluorescent substance, a first measurement of irradiating an excitation light in a first particular wavelength region to said extracted and separated liquid thereby measuring fluoresence intensity in a second particular wavelength region emitted from extracted and separated liquid, thereby obtaining a first measured value, and a second treatment, comprising a second separation of applying said solid-liquid separating procedure for removing solid particles greater than said predetermined particle size, to a second fraction of the Methanogens-containing sample, thereby obtaining a solid-liquid separated liquid, a second extraction by applying heat to said solid-liquid separated liquid thereby obtaining a separated and extracted liquid, a second measurement of irradiating an excitation light in said first particular wavelength region to said separated and extracted liquid, a second measurement of irradiating an excitation light in said first particular wavelength region to said separated and extracted liquid, thereby measuring fluorescence intensity in said second particular wavelength region radiated from said separated and extracted liquid, thereby obtaining a second measured value, and performing a predetermined data processing based on the first and the second measured values thereby obtaining a calculated value for the viability of Methanogens in said Methanogens-containing sample.

25. A method for measuring viability of Methanogens as defined in claim 24, wherein the second separation is conducted subsequent to the first measurement.

26. A method for measuring viability of Methanogens as defined in claim 24, wherein the first extraction is conducted subsequent to the second measurement.

27. A method for measurement viability of Methanogens as defined in claim 24, wherein the first treatment from the first extraction to the first measurement and the second separation to the second measurement are carried out in parallel.

28. A method for measuring viability of Methanogens as defined in claim 24, wherein filtration is applied as the solid-liquid separating procedure.

29. A method measuring viability of Methanogens as defined in claim 24, wherein centrifugal separation is applied as the solid-liquid separating procedure.

30. A method for measuring viability of Methanogens as defined in claim 24, wherein dialysis is applied as the solid-liquid separating procedure.

31. A method for measuring viability of Methanogens as defined in claim 24, wherein the first and second measured values are obtaining by using an excitation light of a single wavelength as the excitation light in the first particular wavelength region in the first and the second measurements, and said first and second measured values are substituted into calculation formulas containing predetermined measured values for the intensity of the fluoresence as the variant, thereby obtaining calculated values in the data processing.

32. A method for measuring viability of Methanogens as defined in claim 24, wherein the first and second measured values each in plurality are obtained by using excitation light in the first wavelength region in the first and the second measurements, and said first and second measured values each in plurality are substituted into calculation formulas containing predetermined measured values for the intensity of each fluorescence relative to each of the wavelengths for said excitation light as the variant thereby obtaining calculated values in the data processing.

* * * * *

UNITED STATES PATENT AND TRADEMARK OFFICE
CERTIFICATE OF CORRECTION

PATENT NO. : 4,898,833

DATED : February 6, 1990

INVENTOR(S) : Satoshi Ueyama, et al

It is certified that error appears in the above-identified patent and that said Letters Patent is hereby corrected as shown below:

Col. 1, line 10, delete "Methanogens containing" and substitute therefore --Methanogens-containing--;

Col. 8, line 41, insert --21-- after "pipe";

Col. 8, line 55, insert --period-- after "predetermined";

Col. 15, line 43, delete "soIution" and substitute therefor --solution--;

UNITED STATES PATENT AND TRADEMARK OFFICE
CERTIFICATE OF CORRECTION

PATENT NO. :   4,898,833

DATED      :   February 6, 1990

INVENTOR(S) :  Satoshi UEYAMA and Satoru ISODA

It is certified that error appears in the above-identified patent and that said Letters Patent is hereby corrected as shown below:

Column 16, line 2, insert -- is applied -- after "separation";

Column 17, line 13, delete "measurement" and substitute therefor -- measuring --;

Column 18, line 6, delete "obtaining" and substitute therefor -- obtained --.

Signed and Sealed this

Fourth Day of June, 1991

Attest:

HARRY F. MANBECK, JR.

*Attesting Officer*      Commissioner of Patents and Trademarks